US009988352B2

(12) United States Patent
Trail et al.

(10) Patent No.: US 9,988,352 B2
(45) Date of Patent: Jun. 5, 2018

(54) COMPOUNDS FOR INHIBITION OF FUNGAL TOXIN PRODUCTION

(71) Applicant: Board of Trustees of Michigan State University, East Lansing, MI (US)

(72) Inventors: Frances Trail, Mason, MI (US); A. Daniel Jones, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days. days.

(21) Appl. No.: 15/316,647

(22) PCT Filed: Jun. 5, 2015

(86) PCT No.: PCT/US2015/034543
§ 371 (c)(1),
(2) Date: Dec. 6, 2016

(87) PCT Pub. No.: WO2015/188136
PCT Pub. Date: Dec. 10, 2015

(65) Prior Publication Data

US 2017/0183309 A1 Jun. 29, 2017

Related U.S. Application Data

(60) Provisional application No. 62/008,673, filed on Jun. 6, 2014.

(51) Int. Cl.

| | |
|---|---|
| ***A01N 37/38*** | (2006.01) |
| ***A01N 43/36*** | (2006.01) |
| ***A01N 43/38*** | (2006.01) |
| ***C07D 211/76*** | (2006.01) |
| ***A01N 43/40*** | (2006.01) |
| ***C07D 211/32*** | (2006.01) |

(52) U.S. Cl.
CPC ............ *C07D 211/76* (2013.01); *A01N 43/40* (2013.01); *C07D 211/32* (2013.01)

(58) Field of Classification Search
None
See application file for complete search history.

(56) References Cited

U.S. PATENT DOCUMENTS

| | | | |
|---|---|---|---|
| 4,474,816 | A | 10/1984 | Wilson, Jr. et al. |
| 6,825,216 | B1 | 11/2004 | Trail et al. |

FOREIGN PATENT DOCUMENTS

| | | | |
|---|---|---|---|
| CN | 102503851 | A | 6/2012 |
| WO | WO-9620595 | A1 | 7/1996 |
| WO | WO-2011069444 | A1 | 6/2011 |
| WO | WO-2013000673 | A1 | 1/2013 |
| WO | WO-2015188136 | A1 | 12/2015 |
| WO | WO-2015188136 | A8 | 12/2015 |

OTHER PUBLICATIONS

"International Application Serial No. PCT/US2015/034543, International Search Report dated Nov. 10, 2015", 7 pgs.
"International Application Serial No. PCT/US2015/034543, Invitation to Pay Add'l Fees and Partial Search Rpt dated Aug. 24, 2015", 8 pgs.
"International Application Serial No. PCT/US2015/034543, Written Opinion dated Nov. 10, 2015", 10 pgs.
Huang, Guang-Ying, et al., "Synthesis and characteristics of (Hydrogenated) ferulic acid derivatives as potential antiviral agents with insecticidal activity", Chemistry Central Journal, 7: 33, (2013), 12 pgs.
Mahmoud, A L, et al., "Antifungal action and antiafiatoxigenic properties of some essential oil constituents", Letters in Applied Microbiology, Published for the Society for Applied Bacteriology by Blackwell Scientific Publications vol. 19, No. 2, (Aug. 1, 1994), 110-113.
Nomura, Eisaku, et al., "Synthesis of Amide Compounds of Ferulic Acid, and Their Stimulatory Effects of Insulin Sevretion In Vitro", Bioorganic & Medicinal Chemistry, 11, (2003), 3807-3813.
Sung-Fun, et al., "Inhibition of Aflatoxin B1 Biosynthesis by Piperlongumine Isolated from Piper longum L", J. Microbiol. Biotechnol vol. 12, No. 4, (Jan. 1, 2002), 679-682.

*Primary Examiner* — Zinna Northington Davis
(74) *Attorney, Agent, or Firm* — Schwegman Lundberg & Woessner, P.A.

(57) ABSTRACT

The invention relates to compounds, compositions, and methods that can inhibit the biosynthesis of mycotoxins.

3 Claims, 1 Drawing Sheet

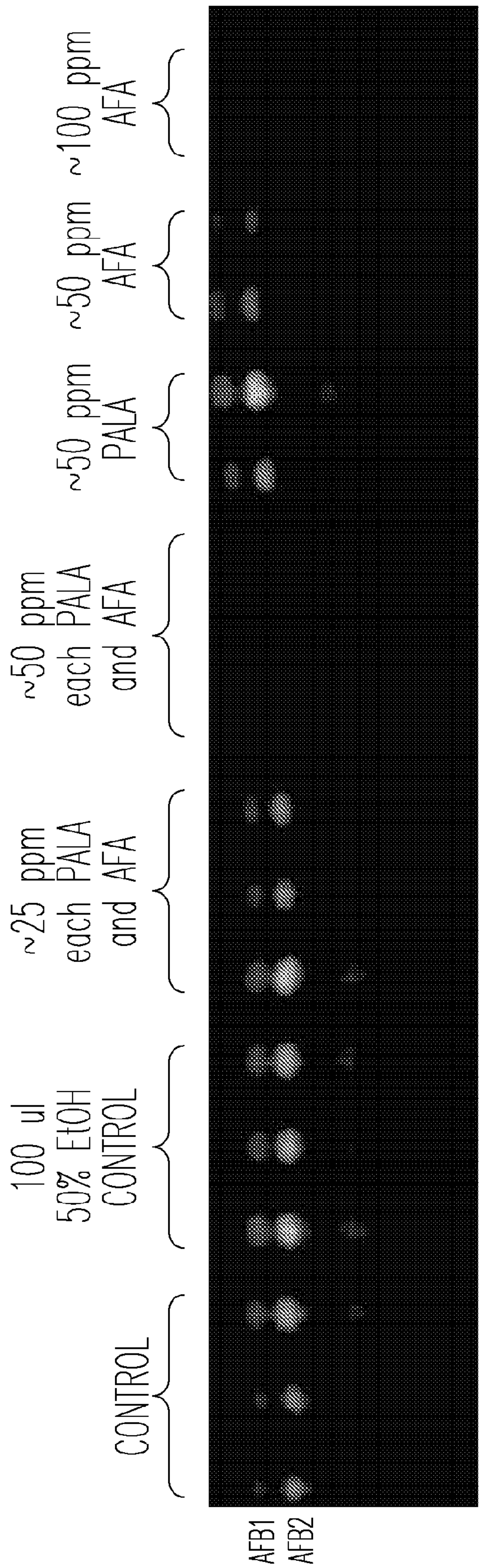
~100 ppm AFA
~50 ppm AFA
~50 ppm PALA
~50 ppm each PALA and AFA
~25 ppm each PALA and AFA
100 ul 50% EtOH CONTROL
CONTROL
AFB1
AFB2

COMPOUNDS FOR INHIBITION OF FUNGAL TOXIN PRODUCTION

PRIORITY APPLICATIONS

This application is a U.S. National Stage Application filed under 35 U.S.C. § 371 from International Application No. PCT/US2015/034543, filed on Jun. 5, 2015, and published as WO 2015/188136 on Dec. 10, 2015, which applications claim the benefit of priority to U.S. Provisional Patent Application Ser. No. 62/008,673, filed Jun. 6, 2014, and which applications and publications are incorporated herein by reference in their entireties.

BACKGROUND

Mycotoxins are toxins produced by fungi that contaminate grains and nuts. These toxins cause immunosuppressive, carcinogenic, cytotoxic and teratogenic effects in humans and animals who consume the contaminated grains and nuts. Aflatoxin, the most well-known mycotoxin, is produced by several species of the fungus *Aspergillus* and contaminates corn, tree nuts, cottonseed and peanuts in the southern and western United States. The FDA limits aflatoxin levels in food and feed to 20 ppb, due to its carcinogenic capabilities. Aflatoxin, together with hepatitis C, is associated with high levels of liver cancer in Southeast Asia. Deoxynivalenol, a mycotoxin common in wheat and barley in the U.S. Midwest, is produced by several *Fusarium* species on grain crops, has immunosuppressive effects on humans, and induces feed refusal in animals. The FDA suggests levels of less than 15 ppm deoxynivalenol in finished products for human consumption.

Economic losses due to mycotoxins in the United States are estimated to be between $0.5 and $1.5 billion annually. Fungicides are only partially effective against mycotoxigenic fungi because such fungi are naturally tolerant to many fungicides, and because when stressed by fungicide applications, fungi can respond by producing more of the mycotoxin. Durable host plant resistance is not available, despite many years of intensive breeding. An alternative to these solutions would be a compound or a mixture of compounds that block mycotoxin biosynthesis, especially when mycotoxin levels can be high, even in asymptomatic nuts and grains.

SUMMARY

The invention relates to compounds that inhibit the biosynthesis of mycotoxins and are useful at sites where mold is present or where it may develop. The compounds are also useful in situations involving the growth and storage of agricultural products, where elimination of mycotoxins is desirable. These compounds may function by shutting off fungal genes involved in synthesis of mycotoxins.

One aspect of the invention is a compound of formula IA or IB:

IA

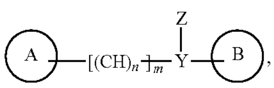

IB

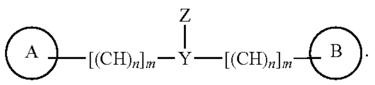

Another aspect of the invention is a compound of formula II:

II

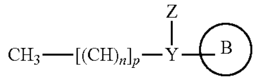

or salts of the compounds of the formulae IA, IB or II; wherein:

ring A is an aryl ring that can have 1-3 substituents, each substituent in place of 1 hydrogen atom, where the substituents are each separately selected from the group consisting of oxo (=O); hydroxy; halogen; lower alkyl; lower alkoxy; amino; thiol; sulfonyl; sulfoxide; and carboxylic acid;

ring B is an aryl or heterocyclic ring that can optionally have 1 or 2 substituents, where the substituents are each separately selected from: oxo (=O); hydroxy; halogen; lower alkyl; lower alkoxy; amino; thiol; sulfonyl; sulfoxide; and carboxylic acid;

Y is a methylene (CH), or a carbon atom (C);

Z is a heteroatom, hydroxy, or amino;

n is an integer equal to 1, 2, or 3;

m is an integer equal to 1, 2, 3, or 4; and p is an integer equal to any of 1-18.

It should be understood that when Y is a carbon atom (C) and Z is a heteroatom, that this combination represents an oxo group (C=O).

Examples of compounds encompassed by the formula IA, IB or II include the following:

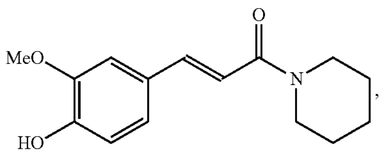

Compound 1: $C_{15}H_{19}NO_3$
Molecular Weight: 261.32

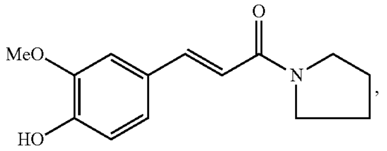

Compound 2: $C_{14}N_{17}NO_3$
Molecular Weight: 247.29

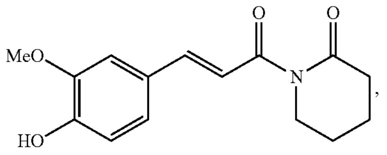

Compound 3: $C_{15}H_{17}NO_4$
Molecular Weight: 275.30

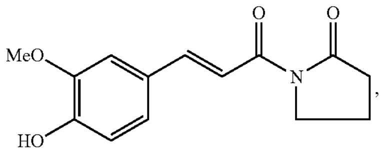

Compound 4: $C_{14}N_{15}NO_4$
Molecular Weight: 261.28

-continued

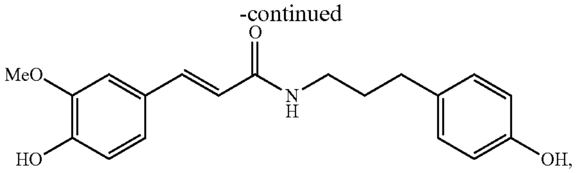

Compound 5: $C_{19}H_{21}NO_4$
Molecular Weight: 327.38

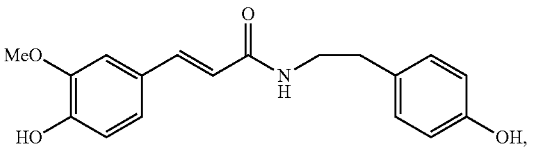

and

Compound 6: $C_{18}H_{19}NO_4$
Molecular Weight: 313.35

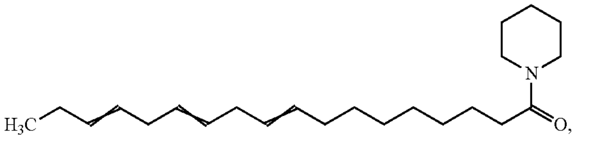

Compound 7 (e.g., 1-piperidin-1-yl)octadeca-9,12,15-trien-1-one), and salts thereof.

Another aspect of the invention is a composition comprising a compound of formula IA, a compound of formula IB, a compound of formula II, or a combination thereof. For example, the composition can include any one of compounds 1-7, or any combination of compounds 1-7.

Another aspect of the invention is a method for inhibiting mycotoxin production by a fungus that includes applying a compound of formula IA, a compound of formula IB, a compound of formula II, or a combination thereof, to the fungus or to a surface (or object) that could have a fungus. For example, any of compounds 1-7 (or combinations thereof) can be applied to a surface or an object to inhibit mycotoxin production by a fungus that may be present on or in the surface or the object.

DESCRIPTION OF THE DRAWING

FIG. 1 is a thin-layer chromatography (TLC) plate on which accumulated aflatoxins B1 and B2 have been separated from liquid cultures of *A. parasiticus* exposed to different levels of ferulic acid derivative (AFA; compound 3) and piperidine amide derivative of linolenic acid (PALA; compound 7). Compounds were delivered to growing cultures in 70% ethanol (EtOH). The lowest row of spots is where 10 uL aliquots of fungal cultures were placed.

DETAILED DESCRIPTION

The invention relates to compounds, compositions, and methods that inhibit the expression of mycotoxin (e.g., aflatoxin) biosynthetic genes in fungi such as *Aspergillus parasiticus* without inhibiting the growth of the fungus. Most economic damage is due to the presence of the mycotoxin, not the presence of the fungus. Accordingly, the compounds, compositions and methods described herein are useful for inhibiting mycotoxin synthesis without destroying potentially useful fungi.

Inhibitors of Mycotoxin Biosynthesis

Compounds that can inhibit mycotoxin biosynthesis include those with formulae IA, IB, and/or II, and salts thereof:

IA

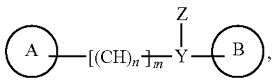

IB

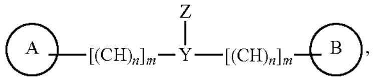

II

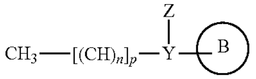

wherein:

ring A is an aryl ring that can have 1-3 substituents, where the substituents can each be separately selected from the group: oxo hydroxy; halogen; lower alkyl; lower alkoxy; amino; thiol; sulfonyl; sulfoxide; and carboxylic acid;

ring B is an aryl or heterocyclic ring that can optionally have 1 or 2 substituents, each substituent in place of 1 or 2 hydrogen atoms, where the substituents are each separately selected from the group consisting of oxo (═O); hydroxy; halogen; lower alkyl; lower alkoxy; amino; thiol; sulfonyl; sulfoxide; and carboxylic acid;

Y is a methylene (CH), or a carbon atom (C);

Z is a heteroatom, hydroxy, or amino;

n is an integer equal to 1, 2, or 3;

m is an integer equal to 1; 2, 3, or 4;

p is an integer equal to any of 1-18.

It should be understood that when Y is a carbon atom (C) and Z is a heteroatom, that this combination represents an oxo group (C═O).

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Heterocyclic groups include aromatic and non-aromatic ring compounds containing three or more ring atoms, of which, one or more is a heteroatom such as, but not limited to, N, O, and S. The heteroatom can, for example, be a nitrogen atom. In some embodiments, heterocycle groups include 3 to about 20 ring atoms, whereas other such groups have 3 to about 15 ring atoms. A heterocycle group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocycle ring can also include one or more double bonds. A heteroaryl ring is an embodiment of a heterocycle group. The phrase "heterocycle group" includes fused ring species including those comprising fused aromatic and non-aromatic groups. For example, a dioxolanyl ring and a benzdioxolanyl ring system (methylenedioxyphenyl ring system) are both heterocycle groups within the meaning herein. The phrase also includes polycyclic ring systems containing a heteroatom such as, but not limited to, quinuclidyl. Heterocyclic groups can be unsubstituted, or can be substituted as discussed above. Heterocyclic groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocycle groups can be mono-substituted or substituted more than once, such as, but not limited to, piperidinyl or quinolinyl groups, which are 2-, 3-, 4-, 5-, or 6-substituted, or disubstituted with groups such as those listed above.

In some embodiments, the heterocyclic ring is a non-aromatic ring with one or two heteroatoms. For example, the heterocyclic ring can be a non-aromatic ring with one heteroatom. The heteroatom can, for example, be oxygen or nitrogen. The B ring can, in some instances, be linked directly to the Y group. In some instances, the B ring can be linked to the Y group via the heteroatom. Alternatively, the heteroatom is a ring atom that is not directly linked to the Y group. In some embodiments, the heterocyclic ring is a non-aromatic ring with one nitrogen heteroatom.

In some embodiments, m is 2 or 3. In some instances, p is an integer of 10-17, or 12-17, or 14-16, or 16.

The compounds of formula II can have 1, 2, 3, or more double bonds, each separately having a cis or a trans configuration.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Lower alkyl groups have about 1 to about 3 carbon atoms. The term "alkylene" means a chain of methylene ($CH_x$) residues, where x is 1 or 2, and where each end of the chain is linked to another moiety.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein. A lower alkoxy group has about 1 to about 3 carbon atoms.

An "amino" group is a substituent of the form $—NH_2$, —NHR, $—NR_2$, $—NR_3^+$, and protonated forms of each, wherein each R is independently selected from a hydrogen or a lower alkyl group.

"Halogen" as the term is used herein includes fluoro, chloro, bromo, and iodo.

All chiral, diastereomeric, racemic forms of a structure are intended to be embraced by the claims, unless the specific stereochemistry or isomeric form is specifically indicated. Compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

The term "salt" generally refers to forms of a compound derived from contacting the compound with an organic or inorganic acid, such as hydrochloric acid, hydrobromic acid, tartaric acid, methylsulfonic acid, acetic acid, maleic acid, and oxalic acid, to form the hydrochloride, hydrobromide, tartarate, methylsulfonate, acetate, maleate, and oxalate salt of the compound. The term "salt" also generally refers to forms of a compound derived from contacting the compound with a base to form, for example, the sodium, potassium, calcium, magnesium, ammonium, and tetraalkylammonium salt of the compound.

Some specific examples of compounds that can inhibit the biosynthesis of mycotoxins, which compounds are encompassed by the formula IA, IB or II, include the following:

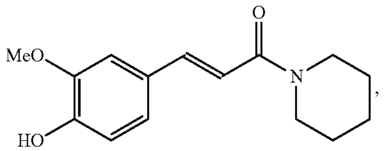

Compound 1: $C_{15}H_{19}NO_3$
Molecular Weight: 261.32

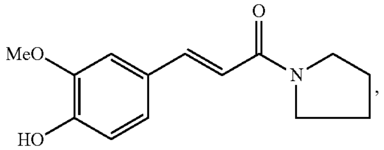

Compound 2: $C_{14}N_{17}NO_3$
Molecular Weight: 247.29

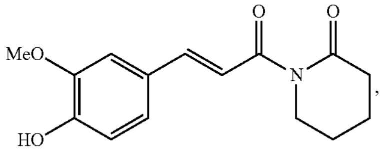

Compound 3: $C_{15}H_{17}NO_4$
Molecular Weight: 275.30

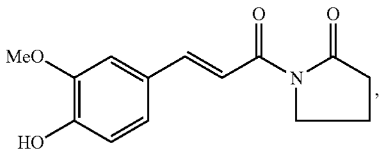

Compound 4: $C_{14}N_{15}NO_4$
Molecular Weight: 261.28

-continued

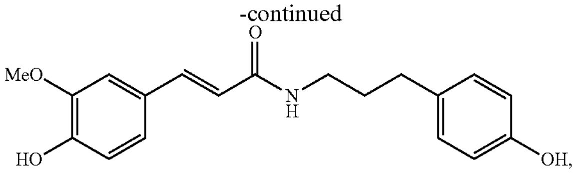

Compound 5: $C_{19}H_{21}NO_4$
Molecular Weight: 327.38

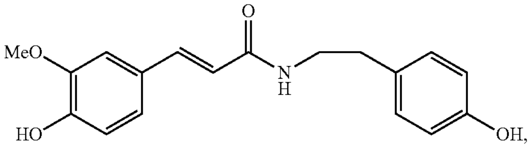

and

Compound 6: $C_{18}H_{19}NO_4$
Molecular Weight: 313.35

Compound 7

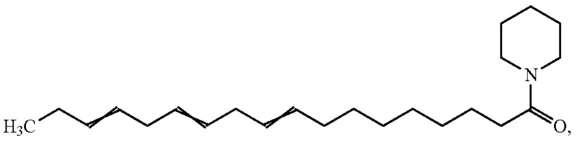

(e.g., 1-piperidin-1-yl)octadeca-9,12,15-trien-1-one)

and combinations thereof. The crossed double bonds ()

in compound 7 indicate that the double bond can have a trans or cis configuration.

Mycotoxin Inhibitor Identification

Several compounds were designed that can eliminate mycotoxin biosynthesis. Such compounds are effective in controlling biosynthesis of deoxynivalenol. In some instances, the compounds do not have fungicidal activity. Hence, beneficial fungi may be unaffected by the compounds, compositions, and methods described herein. Moreover, fungi may not become resistant to the compounds, compositions, and methods described herein; and these compounds may face lower regulatory barriers.

To identify structures of active compounds, compounds were tested for inhibitory activity on aflatoxin biosynthesis in a culture of *Aspergillus parasiticus*. Several compounds from the cultures exhibiting reduced biosynthesis of aflatoxin were identified by mass spectrometry.

Mycotoxins

The compounds, compositions, and methods described herein can inhibit biosynthesis of a variety of mycotoxins.

Mycotoxins are toxic fungal metabolites, often found in agricultural products that are characterized by their ability to cause health problems for humans and vertebrates. Mycotoxins include compounds such as aflatoxins, ochratoxins, patulin, fumonisins, zearalenones, and trichothecenes. They are produced for example by different *Fusarium, Aspergillus, Penicillium* and *Alternaria* species.

Aflatoxins are toxins produced by *Aspergillus* species that grow on several crops, in particular on maize or corn before and after harvest of the crop as well as during storage. The biosynthesis of aflatoxins involves a complex polyketide pathway starting with acetate and malonate. One important intermediate is sterigmatocystin and O-methylsterigmatocystin which are direct precursors of aflatoxins. Important producers of aflatoxins are *Aspergillus flavus*, most strains of *Aspergillus parasiticus, Aspergillus nomius, Aspergillus bombycis, Aspergillus pseudotamarii, Aspergillus ochraceoroseus, Aspergillus rambelli, Emericella astellata, Emericella venezuelensis, Bipolaris* spp., *Chaetomium* spp., *Farrowia* spp., and *Monocillium* spp., in particular *Aspergillus flavus* and *Aspergillus parasiticus* (Plant Breeding (1999), 118, pp 1-16). There are also additional *Aspergillus* species known. The group of aflatoxins consists of more than 20 different toxins, for example, aflatoxin BI, B2, GI and G2, cyclopiazonic acid (CPA).

Ochratoxins are mycotoxins produced by some *Aspergillus* species and *Penicilium* species, like *A. ochraceus, A. carbonarius* or *P. viridicatum*, Examples for Ochratoxins are ochratoxin A, B, and C. Ochratoxin A is the most prevalent and relevant fungal toxin of this group.

Fumonisins are toxins produced by *Fusarium* species that grow on several crops, mainly corn, before and after harvest of the crop as well as during storage. The diseases, *Fusarium* kernel, ear and stalk rot of corn, is caused by *Fusarium verticillioides, Fusarium subglutinans, Fusarium moniliforme*, and *Fusarium proliferatum*. The main mycotoxins of these species are the fumonisins, of which more than ten chemical forms have been isolated. Examples for fumonisins are FB I, FB2 and FB3. In addition the above mentioned *Fusarium* species of corn can also produce the mycotoxins moniliformin and beauvericin. In particular *Fusarium verticillioides* is mentioned as an important pathogen of corn, this *Fusarium* species produces as the main mycotoxin fumonisins of the B-type. Trichothecenes are those mycotoxins of primary concern which can be found in *Fusarium* diseases of small grain cereals like wheat, barley, rye, triticale, rice, sorghum and oat. They are sesquiterpene epoxide mycotoxins produced by species of *Fusarium, Trichothecium*, and *Myrothecium* and act as potent inhibitors of eukaryotic protein synthesis. Some of these trichothecene producing *Fusarium* species also infect corn or maize.

Examples of trichothecene mycotoxins include T-2 toxin, HT-2 toxin, isotrichodermol, diacetoxyscirpenol (DAS), 3-deacetylcalonectrin, 3, 15-dideacetylcalonectrin, scirpentriol, neosolaniol; 15-acetyldeoxynivalenol, 3-acetyldeoxynivalenol, nivalenol, 4-acetylnivalenol (fusarenone-X), 4, 15-diacetylnivalenol, 4,7,15-acetylnivalenol, and deoxynivalenol ("DON") and their various acetylated derivatives. The most common trichothecene in *Fusarium* head blight is deoxynivalenol produced for example by *Fusarium graminearum* and *Fusarium culmorum*.

Another mycotoxin mainly produced by *F. culmorum, F. graminearum* and *F. cerealis* is zearalenone, a phenolic resorcyclic acid lactone that is primarily an estrogenic fungal metabolite.

*Fusarium* species that produce mycotoxins, such as fumonisins and trichothecenes, include *F. acuminatum, F. crookwellense, F., verticillioides, F. culmorum, F. avenaceum, F. equiseti, F. moniliforme, F, graminearum* (*Gibberella zeae*), *F. lateritium, F. poae, F. sambucinum* (*G. pulicaris*), *F. proliferatum, F. subglutinans, F. sporotrichioides* and other *Fusarium* species.

In contrast the species *Microdochium nivale* also a member of the so-called *Fusarium* complex is known to not produce any mycotoxins. Both acute and chronic mycotoxicoses in farm animals and in humans have been associated with consumption of wheat, rye, barley, oats, rice and maize contaminated with *Fusarium* species that produce trichothecene mycotoxins. Experiments with chemically pure trichothecenes at low dosage levels have reproduced many of the features observed in moldy grain toxicoses in animals, including anemia and immunosuppression, hemorrhage, emesis and feed refusal. Historical and epidemiological data from human populations indicate an association between certain disease epidemics and consumption of grain infected with *Fusarium* species that produce trichothecenes. In particular, outbreaks of a fatal disease known as alimentary toxic aleukia, which has occurred in Russia since the nineteenth century, have been associated with consumption of over-wintered grains contaminated with *Fusarium* species that produce the trichothecene T-2 toxin. In Japan, outbreaks of a similar disease called akakabi-byo or red mold disease have been associated with grain infected with *Fusarium* species that produce the trichothecene, DON. Trichothecenes were detected in the toxic grain samples responsible for recent human disease outbreaks in India and Japan. There exists, therefore, a need for agricultural methods for preventing, and crops having reduced levels of, mycotoxin contamination. Further, mycotoxin-producing *Fusarium* species are destructive pathogens and attack a wide range of plant species. The acute phytotoxicity of mycotoxins and their occurrence in plant tissues also suggests that these mycotoxins play a role in the pathogenesis of *Fusarium* on plants. This implies that mycotoxins play a role in disease and, therefore, reducing their toxicity to the plant may also prevent or reduce disease in the plant. Further, reduction in disease levels may have the additional benefit of reducing mycotoxin contamination on the plant and particularly in grain where the plant is a cereal plant.

*Stachybotrys* spp., known as the toxic black molds in buildings, produce trichothecene and atranone mycotoxins that affect human health. These products could be used in paints or plasterboard to inhibit the growth and sporulaiton of *Stachybotrys* in damp building environments.

The compounds of formulae IA, IB, and/or II can be used to inhibit biosynthesis of such mycotoxins.

Plants, Seeds, and Plant Products

Plants, seeds, and plant products can be treated with the compounds and/or compositions described herein. For example, the compounds and/or compositions described herein can be applied to agricultural plants, seeds, and plant products as well as any crops for inhibiting mycotoxin production. In addition, plants grown in nature or for decorative purposes can be treated with the compounds and/or compositions described herein. The plants, seeds, and plant products so treated can be for human or animal consumption.

Plants, or seeds from such plants, for example, can be grain-producing, nut-producing, vegetable-producing, fruit-producing, starch-producing, fiber-producing, fodder-producing, or a combination thereof. The plant products can include grains, nuts, vegetables, fruits, starch, fibers, flour, fodder, leaves, stock, seeds, oil, or a combination thereof. For example, the plant products can be almonds, barley, betel nuts, brazil nuts, cashews, chestnuts, cocoanut, coffee, corn, flour, hazelnuts, macadamia nuts, oats, pecans, peanuts, pine nuts, pistachios, rice, rye, sesame seeds, soybean, spices, walnuts, wheat, or combinations thereof.

Plants can also include vegetables, such as tomatoes, peppers, cabbage, broccoli, asparagus, squash, lettuce, spinach, cauliflower, melon, watermelon, cucumbers, carrots, onions, cucurbits and potatoes, tobacco, pome and stone fruits and berries, such as walnuts, kiwi, banana, avocado, olives, passion fruit, almonds, pineapples, apples, pears, raspberry, cherry, plums, peaches, and cherries, table and wine grapes, citrus fruit, such as oranges, lemons, grapefruits and limes, corn, cotton, soybean, oil seed rape, wheat, barley, rye, triticale, oats, maize, sorghum, sunflower, peanuts, rice, sugar beet, fodder beet, coffee, beans, peas, yucca, sugar cane, clover, turf and ornamentals such as roses.

Additional types of plants, seeds, and plant products can be or can be from flax, cotton, cereals (wheat, barley, rye, oats, millet, triticale, maize (including field corn, popcorn and sweet corn), rice, sorghum and related crops); beet (sugar beet and fodder beet); sugar beet, sugar cane, leguminous plants (beans, lentils, peas, soybeans); oil plants (rape, mustard, sunflowers), *Brassica* oilseeds such as *Brassica napus* (e.g. canola), *Brassica rapa, B. juncea* (e.g. mustard) and *Brassica carinata*; cucumber plants (marrows, cucumbers, melons); fiber plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. commutate Gaud.), sheep fescue (*Festuca* ovine L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia* Willd.), St. Augustinegrass (*Stenotaphrum secundatum* (Walt.) Kuntze); and centipedegrass (*Eremochloa ophiuroides* (Munro.) Hack.)); vines; various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, Brussel sprouts, pak choi, kohlrabi, radish, horseradish, cress, Chinese cabbage), *Leguminosae* sp. (for instance peanuts, peas and beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

Fungi

The compositions described herein can inhibit mycotoxin biosynthesis by a variety of fungi.

For example, the fungi can be of one or more of the classes Ascomycetes, Basidiomycetes, Deuteromycetes, and Oomycetes, such as *Achlya conspicua* (Water-mold), *Achlya klebsiana* (Water-mold), *Aecidium cantensis* (Deforming rust), *Akaropeltopsis* sp. (Sooty blotch), *Albugo tragopogonis* (White rust), *Alternaria alternata* (*Alternaria* rot, Black mold rot, Black shoulder, Brown spot and Black pit, *Alternaria* leaf spot, *Alternaria* leaf blight, stem spot and head rot, Albinism), *Alternaria alternata* f.sp. *Lycopersici* (*Alternaria* stem canker), *Alternaria brassicae* (*Alternaria* leaf spot), *Alternaria brassicicola* (*Alternaria* leaf spot), *Alternaria citri* (*Alternaria* leaf spot of rough lemon, *Alternaria* stem-end rot, Black rot), *Alternaria helianthi* (*Alternaria* leaf blight, stem spot and head rot), *Alternaria helianthicola* (*Alternaria* leaf blight, stem spot and head rot), *Alternaria leucanthemi* (*Alternaria* leaf blight, stem spot and head rot), *Alternaria limicola* (Mancha foliar de los citricos), *Alternaria padwickii* (Stackburn), *Alternaria solani* (Early blight), *Alternaria* spp. (Kernel blight=black point), *Alternaria tenuissima* (*Alternaria* leaf blight, stem spot and head rot), *Alternaria zinnia* (*Alternaria* leaf blight, stem spot and head rot), *Angiosorus solani* (Thecaphora smut), *Armillaria mellea* (*Armillaria* root rot, Mushroom root rot=shoestring root rot or oak root fungi), *Armillaria tabescens* (*Clitocybe* root rot), *Arthrinium arundinis* (Kernel blight=black point), *Ascochyta graminea* (*Ascochyta* leaf spot), *Ascochyta hordei* (*Ascochyta* leaf spot), *Ascochyta sorghi* (*Ascochyta* leaf spot), *Ascochyta tritici* (*Ascochyta* leaf spot), *Ashbya gossypii* (Dry rot (fruit)), *Aspergillus flavus* (Albinism), *Aspergillus niger* (*Aspergillus* rot, Black mold rot), *Asteridiella perseae* (Black mildew), *Bipolaris sorokiniana* (Leaf spots), *Blumeriella jaapii* (leaf spot), *Botryodiplodia* spp. (Fruit rot), *Botryosphaeria disrupta* (Branch canker), *Botryosphaeria dothidea* (Cane blight canker), *Botryosphaeria* obtuse (Branch canker, Fruit rot), *Botryosphaeria quercuum* (Branch canker, Fruit rot), *Botryosphaeria rhodina* (Branch canker, Fruit rot), *Botryosphaeria ribis* (Cane blight canker, *Dothiorella gummosis* and rot), *Botrytis cinerea* (Fruit rot, Gray Mold, *Botrytis* blight, *Botrytis* head rot, *Botrytis* blossom and twig blight, *gummosis*, Gray mold), *Bremia lactucae* (Downy mildew), *Ceratobasidium oryzae-sativae* (Aggregate sheath spot), *Cercospora kikuchii* (Leaf Blight), *Cercospora janseana* (Narrow brown leaf spot), *Cercospora rosicola* (*Cercospora* leaf spot), *Cercospora sojina* (Leaf spot), *Chalara thielavioides* (Black mold), *Choanephora cucurbitarum* (*Choanephora* blight), *Claviceps purpurea* (Ergot), *Cochliobolus miyabeanus* (Brown spot), *Cochliobolus sativus* (Common root rot, crown rot and seedling blight, Kernel blight=black point, Spot blotch), *CoUetotrichum truncatum* (Leaf blight), *Coleosporium helianthi* (Yellow rust), *Coleosporium pacificum* (Yellow rust), *CoUetotrichum acutatum* (Post bloom fruit drop), *CoUetotrichum cereale* Manns (Anthracnose), *CoUetotrichum coccodes* (Anthracnose, Black dot), *CoUetotrichum dematium* (Anthracnose), *CoUetotrichum gloeosporioides* (Anthracnose, Fruit rot, Rusty blight), *Coniothyrium rosarum* (Graft canker), *Coniothyrium wernsdorffiae* (Brand canker), *Corticium stevensii* (Thread blight), *Corynespora cassiicola* (Target spot), *Cryptosporella umbrina* (Brown canker), *Cryptosporium minimum* (Fungal canker), *Curvularia lunata* (Black kernel), *Cylindrocladium scoparium* (Fruit rot, Crown canker), *Dematophora necatrix* (Root rot), *Diapleella coniothyrium* (Common stem canker), *Diaporthe citri* (Melanose), *Diaporthe eres* (Fungal canker), *Didymella applanata* (Spur blight), *Didymella lycopersici Didymella* (Stem rot), *Diplocarpon rosae* (Black spot), *Diplodia cacaoicola* (Dieback), *Diplodia* sp. (Fungal canker), *Discostroma corticola* (Cane blight canker), *Dothiorella aromatic* (Fruit rot), *Dothiorella gregaria* (Fruit rot), *Drechslera gigantean* (Eyespot), *Drechslera teres* (Net blotch), *Drechslera teres* f. maculate (Net blotch (spot form)), *Drechslera wirreganensis* (Wirrega blotch), *Elsinoe ampelina* (Anthracnose and bird's-eye rot), *Elsinoe australis* (Sweet orange scab), *Elsinoe fawcettii* (Scab), *Elsinoe rosarum* (Spot anthracnose), *Entyloma oryzae* (Leaf smut), *Erysiphe cichoracearum* (Powdery mildew), *Erysiphe graminis* (Powdery mildew), *Erythricium salmonicolor* (Pink disease), *Fomitella supine* (Wood rots), *Fulvia fulva* (Leaf mold), *Fusarium culmorum* (Common root rot, crown rot and seedling blight), *Fusarium decemcellulare* (Fruit rot), *Fusarium equiseti* (*Fusarium* stalk rot), *Fusarium graminearum* (Common root rot, crown rot and seedling blight), *Fusarium graminearum* (Scab=head blight), *Fusarium moniliforme* (*Fusarium* wilt), *Fusarium oxysporum* (*Fusarium* wilt), *Fusarium oxysporum* f.sp. *citri* (*Fusarium* wilt), *Fusarium oxysporum* f.sp. *lycopersici* (*Fusarium* wilt), *Fusarium oxysporum* f.sp. radicis-*lycopersici* (*Fusarium* crown and root rot), *Fusarium solani* (*Fusarium* stalk rot), *Fusarium* spp. (*Fusarium* dry rot, *Fusarium* wilt, Kernel blight=black point, Root and bark rot, Scab=head blight, *Fusarium* rot (fruit), *Gaeumannomyces graminis* (Crown sheath rot), *Gaeumannomyces graminis* var *tritici* (Take-all), *Galactomyces candidum* (Sour rot), *Ganoderma applanatum* (Heart rot), *Ganoderma brownie* (Heart rot), *Ganoderma lucidum* (Heart rot), *Ganoderma zonatum* (Butt rot), *Geotrichum candidum* (Sour rot), *Geotrichum citri-aurantii* (Sour rot), *Geotrichum klebahnii* (Sour rot), *Gleosporium* spp. (Storage rot), *Gliocladium roseum* (Pink mold), *Gloeodes pomigena* (Sooty blotch), *Glomerella cingulata* (Anthracnose=wither-tip), *Guignardia citricarpa* (Black spot), *Helminthosporium solani* (Silver scurf), *Helminthosporium* spp. (Smudgy spot), *Hendersonula toruloidea* (*Hendersonula* branch wilt, Rio Grande *gummosis*), *Hymenula cerealis* (*Cephalosporium* stripe), *Laetiporus sulphureus* (Wood rots), *Lasiodiplodia theobromae* (Fruit rot, *Diplodia gummosis* and stem-end rot), *Leptosphaeria lindquistii* (*Phoma* black stem), *Leveillula compositarum* f. *helianthi* (Powdery mildew), *Leveillula taurica* (Powdery mildew), *Macrophomina phaseolina* (Charcoal rot), *Magnaporthe salvinii* (Stem rot), *Microdochium nivale* (Pink snow mold=*Fusarium* patch), *Microdochium oryzae* (Leaf scald), *Microdochium tabacinum* (*Fusarium* stalk rot), *Mucor paronychia* (*Mucor* fruit rot), *Mucor racemosus* (*Mucor* fruit rot), *Mycosphaerella angulata* (Angular leaf spot), *Mycosphaerella citri* (Greasy spot and greasy spot rind blotch), *Mycosphaerella horii* (Leaf spot), *Mycosphaerella lageniformis* (Leaf spot), *Mycovellosiella concors* (*Cercospora* leaf blotch), *Myriosclerotinia borealis* (Snow scald=*Sclerotinia* snow mold), *Myrothecium roridum* (*Myrothecium* leaf and stem spot), *Myrothecium verrucaria* (*Myrothecium* leaf and stem spot), *Nectria cinnabarina* (Fungal canker), *Nectria galligena* (collar rot), *Nectria haematococca* (Dry root rot complex), *Nectria pseudotrichia* (Fruit rot), *Nematospora coryli* (Dry rot (fruit)), *Oidiopsis sicula* (Powdery mildew), *Oidium* spp. (Powdery mildew), *Oidium tingitaninum* (Powdery mildew), *Oxyporus latemarginatus* (Heart rot, Poria root rot), *Pellicularia koleroga* (Thread blight), *Penicillium digitatum* (Green mold), *Penicillium italicum* (Blue mold), *Penicillium ulaiense* (Whisker mold), *Peronospora sparsa* (Downy mildew), *Pestalotia adusta* (Leaf spots), *Pestalotia* spp. (Fruit rot, Leaf spots), *Pestalotia versicolor* (Fruit rot), *Phaeoramularia angolensis* (*Phaeoramularia* leaf and fruit spot), *Phialophora asteris* (*Phialophora* yellows), *Phoma andigena* var. *andina* (*Phoma* leaf spot), *Phoma destructive* (*Phoma* rot), *Phoma macdonaldii* (*Phoma* black stem), *Phoma solanicola* f. *foveata* (Gangrene), *Phoma tracheiphila* (Mai secco), *Phomopsis citri* (*Phomopsis* stem-end rot), *Phomopsis helianthi* (*Phomopsis* brown stem canker), *Phomopsis perseae* (Fruit rot), *Phomopsis* spp. (Dieback, *Phomopsis* spot, *Phomopsis* brown stem canker), *Phragmidium mucronatum* (Rust), *Phragmidium rosae-pimpinellifoliae* (Rust), *Phyllachora gratissima* (Leaf spots, Tar spot), *Phyllosticta micropuncta* (Leaf spots), *Phymatotrichopsis omnivore* (*Phymatotrichum* root rot (cotton root rot), *Physalospora abdita* (Branch canker), *Physalospora perseae* (*Physalospora* canker), *Phytophthora capsici* (Buckeye fruit and root rot), *Phytophthora cinnamomi* (*Phytophthora* crown rot, *Phytophthora* root rot, *Phytophthora* trunk canker), *Phytophthora citricola* (*Phytophthora* crown rot, *Phytophthora* trunk canker, Brown rot (fruit)), *Phytophthora citrophthora* (Brown rot (fruit), *Phytophthora* foot rot, *gummosis* and root rot), *Phytophthora drechsleri* (Buckeye fruit and root rot, *Phytophthora* stem rot), *Phytophthora heveae* (*Phytophthora* trunk canker), *Phytophthora hibernalis* (Brown rot (fruit), *Phytophthora* foot rot, *gummosis* and root rot), *Phytophthora infestans* (Late blight), *Phytophthora nicotianae* var. *parasitica* (Buckeye fruit and root rot, Brown rot (fruit), *Phytophthora* foot rot, *gummosis* and root rot), *Phytophthora palmivora* (Seedling blight, Brown rot (fruit), *Phytophthora* foot rot, *gummosis* and root rot), *Phytophthora sojae* (stem and root rot), *Phytophthora* spp. (Pink rot, *Phytophthora* stem rot), *Phytophthora syringae* (Brown rot (fruit), *Phytophthora* foot rot, *gummosis* and root rot), *Plasmopara halstedii* (Downy mildew), *Plasmopara helianthi* f. *helianthi* (Downy mildew), *Plasmopara viticola* (Downy mildew), *Pleospora herbarum* (*Pleospora* rot), *Polyscytalum pustulans* (Skin spot), *Pseudocercosoporella herpotrichoides* (Eyespot), *Pseudocercospora fuligena* (*Cercospora* leaf mold), *Pseudocercospora puderi* (*Cercospora* leaf spot), *Pseudocercospora purpurea* (*Cercospora* spot (blotch)), *Pseudoperonospora cubensis* (Downy mildew), *Pseudopezicula tetraspora* (Angular leaf scorch), *Pseudoseptoria donacis* (Halo spot), *Puccinia coronata* var. *hordei* (Crown rust), *Puccinia graminis* f.sp. *secalis* (Stem rust), *Puccinia graminis* f.sp. *tritici* (Stem rust), *Puccinia helianthi* (Rust), *Puccinia hordei* (Leaf rust), *Puccinia pittieriana* (Common rust), *Puccinia striiformis* f.sp. *Hordei* (Stripe rust=yellow rust), *Puccinia xanthii* (Rust), *Pyrenochaeta lycopersici* (Corky root rot), *Pyrenophora graminea* (Barley stripe), *Pyrenophora teres* (Net blotch), *Pyrenophora tritici-repentis* (Tan spot), *Pyricularia grisea* (Blast), *Pythium aphanidermatum* (*Pythium* damping-off and fruit rot, *Pythium* seedling blight and root rot, Damping-off), *Pythium arrhenomanes* (*Pythium* damping-off and fruit rot, *Pythium* root rot), *Pythium debaryanum* (*Pythium* damping-off and fruit rot, *Pythium* seedling blight and root rot, Damping-off), *Pythium graminicola* (*Pythium* root rot), *Pythium* irregular (*Pythium* seedling blight and root rot), *Pythium iwayamae* (Snow rot), *Pythium myriotylum* (*Pythium* damping-off and fruit rot), *Pythium okanoganense* (Snow rot), *Pythium paddicum* (Snow rot), *Pythium rostratum* (Damping-off, Rootlet rot), *Pythium* spp. (Damping-off, Leak, *Pythium* root rot, *Pythium* seedling blight and root rot), *Pythium tardicrescens* (*Pythium* root rot), *Pythium ultimum* (*Pythium* damping-off and fruit rot, Rootlet rot), *Pythium vexans* (Damping-off), *Rhizoctonia cerealis* (Sharp eyespot), *Rhizoctonia oryzae* (Sheath spot), *Rhizoctonia solani* (Canker and black scurf, Damping-off and fruit rot, Root rot, Seedling blight), *Rhizopus arrhizus* (*Rhizopus* head rot), *Rhizopus* microspores (*Rhizopus* head rot), *Rhizopus stolonifer* (Fruit rot, *Rhizopus* rot, *Rhizopus* head rot), *Rhynchosporium* (Leaf blotch), *Rhytidhysteron rufulum* (Twig blight), *Rigidoporus ulmarius* (Wood rots), *Rosellinia bunodes* (*Rosellinia* root rot), *Rosellinia necatrix* (White root rot), *Rosellinia* spp. (*Rosellinia* root rot, White root rot, *Rosellinia* black rot), *Rosellinia subiculata* (White root rot), *Sarocladium oryzae* (Sheath rot), *Schizothyrium pomi* (Fly speck), *Sclerophthora macrospora* (Downy mildew), *Sclerophthora rayssiae* (Downy mildew), *Sclerotinia minor* (White mold, *Sclerotinia* basal stalk rot and wilt), *Sclerotinia sclerotiorum* (Collar rot, Fruit rot, White mold, *Sclerotinia* basal stalk rot and wilt, mid-stalk rot, head rot, *Sclerotinia* twig blight, fruit rot and root rot), *Sclerotium rolfsii* (Seedling blight, Southern blight, Stem rot), *Septoria citri* (*Septoria* spot), *Septoria helianthi* (*Septoria* leaf spot), *Septoria lycopersici* (*Septoria* leaf spot), *Septoria nodorum* (Glume blotch), *Septoria* passerinii (*Septoria* speckled leaf blotch), *Septoria rosae* (*Septoria* leaf spot), *Septoria tritici* (leaf spot), *Sphaceloma perseae* (Scab (fruit & leaf)), *Sphaeropsis tumefaciens* (Branch knot), *Sphaerotheca fuliginea* (Powdery mildew), *Sphaerotheca pannosa* var. *rosae* (Powdery mildew), *Spongospora subterranea* f.sp. *Subterranea* (Powdery scab), *Stagonospora avenae* f.sp. *triticae* (*Septoria* speckled leaf blotch), *Stagonospora avenae* f.sp. *triticae* (*Stagonospora* blotch), *Stagonospora nodorum* (*Stagonospora* blotch), *Stemphylium botryosum* (Black mold rot), *Stemphylium botryosum* f.sp. *lycopersici* (Gray leaf spot), *Stemphylium lycopersici* (Gray leaf spot), *Stemphylium solani* (Gray leaf spot), *Synchytrium endobioticum* (Wart), *Stemphylium vesicarium* (Brown spot), *Thanatephorus cucumeris* (Sheath blight, Areolate leaf spot), *Thielaviopsis basicola* (Black root rot), *Tilletia barclayana* (Kernel smut), *Tilletia controversa* (Dwarf bunt), *Trametes* hirsute (Wood rots), *Trichoderma viride* (*Trichoderma* rot), *Trichothecium roseum* (Pink rot), *Typhula idahoensis* (Speckled snow mold), *Typhula incarnate* (Gray snow mold=*Typhula* blight), *Typhula ishikariensis* (Gray snow mold=*Typhula* blight), *Ulocladium atrum* (*Ulocladium* blight), *Uromyces junci* (Rust), *Ustilaginoidea virens* (False smut), *Ustilago hordei* (Covered smut), *Ustilago nigra* (False loose smut), *Ustilago nuda* (Loose smut), *Ustulina deusta* (*Ustulina* root rot), *Venturia inaequalis* (Apple scab), *Venturia* Spp. (leaf scabs and blights), *Verticillium albo-atrum* (*Verticillium* wilt), *Verticillium dahlia* (*Verticillium* wilt).

Treatment

Plants, seeds, and plant products can be treated with the compounds and/or compositions described herein. A method can be employed that includes administering any of the compounds or compositions described herein to one or more plants, one or more plant seeds, or one or more plant products.

The compounds described herein can also be applied to structures (e.g., houses, barns, sheds, warehouses, basements, attics, cupboards, storage bins, storage containers, etc.) where mold or fungi is present or may grow. For example, the compounds described herein can be applied to moist areas and/or areas suspected of developing fungal growth. Examples of areas where the compounds and/or compositions can be applied include laundry rooms, bathrooms, bedrooms, closets, basements, attics, kitchens, cabinets, animal pens, storage areas, silos, grain bins, siding, decks, and the like.

Application of compounds or compositions can be carried out directly, or by action on their environment, habitat or storage area. Application (or treatment) methods include, for example, watering (drenching), drip irrigation, spraying, atomizing, broadcasting, dusting, foaming, spreading-on, brushing on, and combinations thereof. Plants, seeds, plant products, surfaces, and/or structure can be treated by powdering, spraying, mixing, encrusting, or a combination thereof. The compositions can be applied in dry or liquid form.

The compounds and compositions described herein can be employed for reducing mycotoxin contamination or in the protection of materials, surfaces, products, and combinations thereof. The compounds or compositions according to the invention can be used to curatively or preventively reduce the mycotoxin synthesis by fungi. For example, a method can be employed for curatively or preventively reducing mycotoxin contamination by use of a composition comprising a compound according to formula I and/or a compound of formula II application to a plant seed, a plant, a plant product, or to the fruit of the plant or to the soil in which the plant is growing or in which it is desired to grow. Suitably, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of seeds, plant cuttings or twigs serving propagation.

The compounds and/or compositions are useful in reducing mycotoxin contamination when they are applied to a plant, plant see, plant product, and/or plant propagation material in an effective amount before and/or after harvest and/or during storage.

An effective amount is an amount sufficient to reduce mycotoxin production by at least about 5%, 10%, 20%, 25%, 30%, 40%, 50%, 60%, 70%, 75%, 80%, 85%, 90%, 93%, 94%, 95%, 96%, 97%, 98%, 99%, 99.5%, or 99.9%. For example, the compounds described herein can each be applied at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm, or about 25 ppm. In some instances, the compounds and/or compositions are provided as concentrated formulation that are diluted ten-fold, 100-fold, or 1000-fold to provide a concentration that is applied to structures, walls, floors, ceilings, containers, plants, seeds, and/or plant products.

The period of time within which protection is effective generally extends from 1 to 90 days, from 1 to 80 days, from 1 to 70 days, from 1 to 60 days, from 1 to 45 days, from 1 to 30 days, from 1 to 14 days, or from 1 to 7 days, after application of the compounds and/or compositions described herein.

At certain application rates, the active compound combinations can, for example, have a strengthening effect in plants. For example, the compounds and/or compositions can also mobilize the defense system of the plant against attack by unwanted phytopathogenic fungi and/or microorganisms and/or viruses. This may, if appropriate, be one of the reasons of the enhanced activity of the combinations according to the invention against biosynthesis of mycotoxins.

Compositions

Compositions are described herein that include at least one compound of formula IA, formula IB, and/or formula II. The compositions can also comprise additional components such as a carrier, solvent, surfactant, an additional active ingredient, or a combination thereof.

The compositions can be dry compositions or liquid compositions. In some instances, the compounds are dissolved in a solvent to form a liquid composition with a known concentration of at least one compound of formula IA, a known concentration of at least one compound of formula IB, and/or a known concentration of at least one compound of formula II. The solvent can be an alcohol. For example, the solvent can be ethanol, methanol, isopropyl alcohol, or a combination thereof.

The compositions can contain an emulsifier, a dispersing agent, thickening agent, a surfactant, a wetting agent of ionic or non-ionic type or a mixture of such agents. For example, the compositions can contain polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulfate, sulfonate and phosphate functions. The presence of at least one surfactant can be included when the active compound and/or the inert support are water-insoluble and when the vector agent for the application is water. For example, surfactant content can be about 5% to 40% by weight of the composition.

Coloring agents such as inorganic pigments can be present in the composition, for example iron oxide, titanium oxide, ferrocyanblue, and organic pigments such as alizarin, azo and metallophthalocyanine dyes, and trace elements such as iron, manganese, boron, copper, cobalt, molybdenum and zinc salts can be used. The compounds can be present in paints along with any available coloring material (s) and other components typically employed in paints.

Optionally, other additional components may also be included, e.g. protective colloids, adhesives, thickeners, thixotropic agents, penetration agents, stabilizers, sequestering agents.

The compositions can also include other ingredients. For example, bactericide compounds can be employed. Such compounds are useful in crop protection for example for controlling Pseudomonadaceae, Rhizobiaceae, Enterobacteriaceae, Corynebacteriaceae and Streptomycetaceae. In addition, the compounds described herein can be used together in a composition or they can be used concomitantly with one or more of the other agrichemicals such as various pesticides, acaricides, nematicides, other types of fungicides, and plant growth regulators.

Other types of fungicides can optionally be included in the compositions described herein. Examples include copper fungicide such as basic copper chloride and basic copper sulfate, sulfur fungicide such as thiuram, zineb, maneb, mancozeb, ziram, propineb, and polycarbamate, polyhaloalkylthio fungicide such as captan, folpet, dichlorfluanid, organochlorine fungicide such as chlorothalonil, fthalide, organophosphorous fungicide such as O,O-bis(1-methylethyl) S-phenylmethyl phosphorothioate (IBP), edifenphos (EDDP), tolclophos-methyl, pyrazophos, fosetyl, dicarboxylmide fungicide such as iprodione, procymidone, vinclozolin, fluoromide, carboxyamide fungicide such as oxycarboxin, mepronil, flutolanil, tecloftalam, trichlamide, pencycuron, acylalanine fungicide such as metalaxyl, oxadixyl, furalaxyl, methoxyacrylate fungicides such as kresoxim-methyl (stroby), azoxystrobin, metominostrobin, trifloxystrobin, pyraclostrobin, anilinopyrimidine fungicide such as andupurine, mepanipyrim, pyrimethanil, cyprodinil, antibiotic agents such as polyoxin, blasticidin S, kasugamycin, validamycine, dihydrostreptomycin sulfate, propamocarb hydrochloride, quintozene, hydroxyisoxazole, methasulfocarb, anilazine, isoprothiolane, probenazole, chinomethionat, dithianon, dinocap, diclomezine, ferimzone, fluazinam, pyroquilon, tricyclazole, oxolinic acid, iminoctadine acetate, iminoctadine albesilate, cymoxanil, pyrrolnitrin, diethofencarb, binapacryl, lecithin, sodium bicarbonate, fenaminosulf, dodine, dimethomorph, phenazine oxide, carpropamid, flusulfamide, fludioxonil, famoxadone, or combinations thereof.

The other type of fungicide can be mixed together and used various amounts with one of the compounds of formula IA, IIB, or II. The compound of formula IA, IB, or II can be used in a weight ratio relative to the other type of fungicide such as from 1:0.001 to 1:1000 as a weight ratio. In some instance, a compound of formula IA, IB, or II relative to the other type of fungicide can vary from 1:0.01 to 1:100 as a weight ratio.

The pesticides can include organophosphorous pesticides, carbamate pesticides such as fenthion, fenitrothion, diazinon, chlorpyrifos, ESP, vamidothion, phenthoate, dimethoate, formothion, malathon, trichlorfon, thiometon, phosmet, dichlorvos, acephate, EPBP, methylparathion, oxydemeton-methyl, ethion, salithion, cyanophos, isoxathion, pyridaphenthion, phosalone, methidathion, sulprofos, chlorfevinphos, tetrachlorvinphos, dimethylvinphos, propaphos, isofenphos, ethylthiometon, profenofos, pyraclofos, monocrotophos, azinphosmethyl, aldicarb, methomyl, thiodicarb, carbofuran, carbosulfan, benfuracarb, furathiocarb, propoxur, BPMC, MTMC, MIPC, carbaryl, pirimicarb, ethiofencarb, and fenoxycarb, pyrethroid pesticides such as permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, ethofenprox, cycloprothrin, tralomethrin, silafluofen, brofenprox, and acrinathrin, and benzoylurea and other types of pesticides such as diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotin sulfate, rotenone, mataldehyde, machine oil, and microbial pesticides e.g. BT and insect pathogenic virus.

The acricides that can be employed include, for example, chlorbenzilate, phenisobromolate, dicofol, amitraz, BPPS, benzomate, hexythiazox, fenbutatin oxide, polynactin, chinomethionat, CPCBS, tetradifon, avermectin, milbemectin, clofentezin, cyhexatin, pyridaben, fenpyroximate, tebufenpyrad, pylidimifen, fenothiocarb, and dienochlor.

As for the aforementioned nematicides, fenamiphos, fosthiazate and the like can be specifically exemplified; as for plant-growth regulators, gibberellins (e.g., gibberellin A3, gibberellin A4, and gibberellin A7), auxin, 1-naphthaleneacetic acid, and so on can be specifically exemplified.

More generally, the active compounds can be combined with any solid or liquid additive, which complies with the usual formulation techniques. In general, the composition according to the invention may contain from 0.05 to 99% by weight of active compounds, preferably from 10 to 70% by weight.

The compounds or compositions can be provided in a form that is ready-to-use or in a form that can be prepared for use. The compounds or compositions can be applied by a suitable device, such by use of a spraying or dusting device. The compounds or compositions can be applied by use of brush or roller. The compounds or compositions can be provided in concentrated commercial compositions that should be diluted before application to the crop. For example, the compounds can provided in dry (e.g., lyophilized) form, or in concentrated form, and then dissolved or diluted as desired. The compositions can be in formulated into an aerosol dispenser, as a capsule suspension, as a cold fogging concentrate, as a dustable powder, as an emulsifiable concentrate, as an emulsion oil in water, as an emulsion water in oil, as an encapsulated granule, as a fine granule, as a flowable concentrate for seed treatment, as a gas (under pressure), as a gas generating product, as granules, as a hot fogging concentrate, as macrogranules, as microgranules, as an oil dispersible powder, as an oil miscible flowable concentrate, as an oil miscible liquid, as a paste, as a plant rodlet, as a powder for dry seed treatment, as seeds coated with the composition, as a soluble concentrate, as a soluble powder, as a solution for seed (or other) treatment, as a suspension concentrate (flowable concentrate), as an ultra-low volume (ULV) liquid, as an ultra-low volume (ULV) suspension, as water dispersible granules or tablets, as a water dispersible powder for slurry treatment, as water soluble granules or tablets, as a water soluble powder for seed treatment, as a wettable powder, or as a combination thereof (e.g., two types of formulations packaged together).

Definitions

The term “contacting,” as used herein, refers to applying the compounds, mixtures and compositions of the invention to an agricultural product, to plants, to plant seeds, to a site of infestation by fungi, to a potential site of infestation by the fungi, which may require protection from infestation, or the environment around the habitat or potential habitat of the fungi. The application may be by methods described in the art such as by spraying, dipping, etc.

As used herein the term “plant” includes reference to whole plants, plant organs (e.g. leaves, stems, twigs, roots, trunks, limbs, shoots, seeds, fruits etc.), or plant cells.

As used herein the term “plant propagation material” includes all the generative parts of the plant such as seeds and vegetative plant material such as cuttings and tubers, which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring. In a particular embodiment, the term propagation material denotes seeds.

Example 1: Materials and Methods

This Example describes some of the materials and methods employed in the development of the invention.

All tests were performed in 24-well plates. Each culture well was filled with 1 mL of low salts medium (LSM) and 10 uL of *A. parasiticus* conidial stock ($5\times10^5$ conidia/ml). Cultures of *A. parasiticus* were placed in the dark for 18 hours before compounds and their solvent vehicles were added to the growing culture.

Solvent Identification

Initial tests were performed to ascertain which solvent was best suited for both dissolving the compounds and that did not prevent growth of *A. parasiticus* were conducted. The solvents tested were as follows:

Methanol at 50, 70, and 100% concentration (diluted with $ddH_2O$);

Ethanol at 50, 70, and 100% concentration (diluted with $ddH_2O$);

Acetone at 50, 70, and 100% concentration (diluted with $ddH_2O$); and

Isopropyl alcohol at 50, 70, and 100% concentration (diluted with $ddH_2O$).

All solvents above were placed into wells containing 1 mL of Low Salts Medium and with 10, 25, or 50 uL of each solvent. Each solvent type was tested in triplicate. Ethanol (50 to 70%) was found to perform best for both dissolving the compounds and for allowing growth of *A. parasiticus*. The presence of acetone in culture appeared in some cases to increase the production of aflatoxin by *A parasiticus*.

Inhibitory Compound Identification

To identify compounds that inhibited mycotoxin biosynthesis, individual and pairwise combinations of compounds were placed in each of the wells and cultures were left in the dark for six additional days. The assays for each compound type were performed in triplicate. Compounds were individually tested at concentrations of parts per thousand (ppt), parts per million (ppm), and parts per billion (ppb) with further refinement of concentrations taking place throughout testing procedures.

To test for the presence of aflatoxin buildup in each well, the mycelial mat was moved to the side of the well with a pipette tip and the liquid medium was stirred to homogenize the sample. Ten microliters (μL) of the incubation medium were withdrawn and spotted onto thin layer chromatography (TLC) plates. The TLC plates were allowed to dry for one hour before development in 95:5 chloroform:acetone within TLC tanks that had equilibrated for one hour. Plates were developed for 15 to 18 minutes, dried, and viewed under ultraviolet light at 254 nm wavelength. Aflatoxin B1 and B2 glowed blue under ultraviolet light and photographs were taken.

All tests were performed with a control that did not contain any of the solvents. One additional control test was performed by adding 10, 25, and 50 uL of sterile water. None of the controls altered aflatoxin production.

Compounds that were successful at limiting or preventing the production of aflatoxin were also tested for their efficacy at preventing the production of deoxynivalenol (DON) in *Fusarium graminearum*. Fungal isolates were grown in identical conditions as used for *Aspergillus*. However, ethanol was the only solvent employed for delivery of the compounds tested with *Fusarium graminearum*. In addition, a larger sample of media was collected for evaluation of *Fusarium graminearum*. Five hundred μL of liquid media was removed from wells to be tested for deoxynivalenol (DON) concentration and lyophilized. DON was not detected by HPLC analysis, which can detect down to ng/sample, in samples treated with AFA or PALA or both.

Note that DON was also not detected when compounds 1 and 2 were tested in combination (but some DON was detected when compounds 1 and 2 were tested alone).

Example 2: Identification of Compounds that Inhibit Mycotoxin Biosynthesis

Two compounds of the eight compounds demonstrated substantial activity in reducing aflatoxin accumulation in liquid cultures of *A. parasiticus*. The first compound was a ferulic acid derivative (AFA; compound 3), shown below.

3

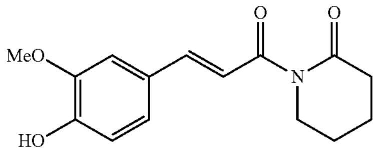 [SMILES: COc1cc(/C=C/C(=O)N2CCCCC2=O)ccc1O]

(E)-1-(3-(4-hydroxy-3-methyoxyphenyl)acryloyl)piperidin-2-one

The second compound was a piperidine amide of linolenic acid (PALA; compound 7), shown below, where the crossed double bonds

indicate that the double bond can have a trans or cis configuration.

(7)

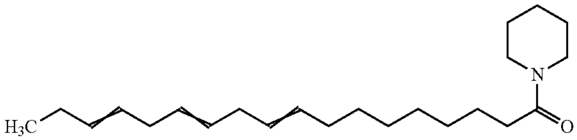

1-piperidin-1-yl)octadeca-9,12,15-trien-1-one

As illustrated in the drawing, the ferulic acid derivative (3) reduced aflatoxin levels up to 80% when used at the lowest effective concentration of 25 ppm as detected by thin layer chromatography (TLC) analysis. The second compound (7) reduced aflatoxin accumulation in culture, but the effect was inconsistent from one trial to the next.

The drawing also shows that when compounds 3 and 7 were used in combination, aflatoxin accumulation was not detectable by TLC. The most effective reduction of aflatoxin occurred when the two compounds were employed together at 50 ppm each. The results indicated that the estimated reduction in aflatoxin accumulation is about 90%-100%.

REFERENCES

Annis, S. L., Velasquez, L., Xu, H., Hammerschmidt, R., Linz, J., & Trail, F. (2000). Novel procedure for identification of compounds inhibitory to transcription of genes involved in mycotoxin biosynthesis. Journal of Agricultural and Food Chemistry, 48(10), 4656-60.

Burow, G. B., Nesbitt, T. C., Dunlap, J. D., and Keller, N. P. 1997. Seed li-poxygenase products modulate *Aspergillus* mycotoxin biosynthesis. Mol. Plant-Microbe Interact. 10:380-387.

Fabbri, A. A., Fanelli, C., Panfili, G., and Passi, S. 1983. Lipoperoxidation and aflatoxin biosynthesis by *Aspergillus parasiticus* and *A. flavus*. J. Gen. Microbiol. 129: 3447-3452.

Fanelli, C., Fabbri, A. A., Finotti, E., and Passi, S. 1983. Stimulation of aflatoxin biosynthesis by lipophilic epoxides. J. Gen. Microbiol. 129:1721-1723.

Goodrich-Tanrikulu, M., Mahoney, N., and Rodriguez, S. B. 1995. The plant growth regulator methyl jasmonate inhibits aflatoxin production by *Aspergillus flavus*. Microbiology. 141:2831-2837.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements:

1. A composition comprising at least one compound of formula IA, at least one compound of formula IB, at least one compound of formula II, or a combination or salt thereof:

IA

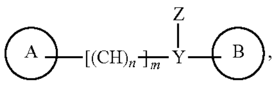

IB

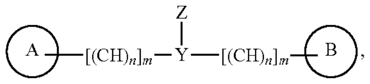

II

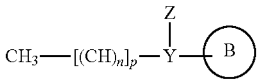

wherein:

ring A is an aryl ring that can have 1-3 substituents, each substituent in place of 1 hydrogen atom, where the substituents are each separately selected from the group consisting of oxo (═O); hydroxy; halogen; lower alkyl; lower alkoxy; amino; thiol; sulfonyl; sulfoxide; and carboxylic acid;

ring B is an aryl or heterocyclic ring that can optionally have 1 or 2 substituents, where the substituents are each separately selected from: oxo (═O); hydroxy; halogen; lower alkyl; lower alkoxy; amino; thiol; sulfonyl; sulfoxide; and carboxylic acid;

Y is a methylene (CH), or a carbon atom (C);

Z is a heteroatom, hydroxy, or amino;

n is an integer equal to 1, 2, or 3;

m is an integer equal to 1, 2, 3, or 4; and p is an integer equal to any of 1-18.

2. The composition of statement 1, wherein the aryl contains about 6 to about 14 carbons in the ring portions of the aryl.
3. The composition of statement 1 or 2, wherein the aryl is phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, or naphthyl.
4. The composition of any of statements 1-3, wherein the aryl is phenyl or naphthyl.
5. The composition of any of statements 1-4, wherein the aryl is phenyl.
6. The composition of any of statements 1-5, wherein two substituents are on ring A.
7. The composition of any of statements 1-6, wherein ring A is phenyl with two substituents.
8. The composition of any of statements 1-7, wherein ring A is phenyl with two substituents, separately at the meta and para positions.
9. The composition of any of statements 1-8, wherein the substituents on the aryl are each separately selected from the group consisting of hydroxy; halogen; lower alkyl; lower alkoxy; amino; and thiol.
10. The composition of any of statements 1-9, wherein the substituents on the aryl are each separately hydroxy or and lower alkoxy.
11. The composition of any of statements 1-10, wherein m is 2, 3, or 4.
12. The composition of any of statements 1-11, wherein m is 2 or 3.
13. The composition of any of statements 1-12, wherein m is 2 or 3, and n is 2 in the $[(CH)_n]_m$ group.
14. The composition of any of statements 1-13, wherein m is 2 or 4, and n is 1 in the $[(CH)_n]_m$ group.
15. The composition of any of statements 1-14, wherein Z is oxo (═O), hydroxy, or amino.
16. The composition of any of statements 1-15, wherein Z is oxo (═O), and Y is a carbon atom.
17. The composition of any of statements 1-16, wherein B is a non-aromatic ring.
18. The composition of any of statements 1-16, wherein B is an aryl ring.
19. The composition of any of statements 1-18, wherein the B ring has 4 to 10 ring atoms.
20. The composition of any of statements 1-19, wherein the B ring has 5 to 7 ring atoms.
21. The composition of any of statements 1-20, wherein the B ring has 6 ring atoms.
22. The composition of any of statements 1-20, wherein the B ring has one or two heteroatoms.
23. The composition of any of statements 1-22, wherein the B ring has one heteroatom.
24. The composition of any of statements 1-22, wherein the B ring has at least one nitrogen or oxygen heteroatom.
25. The composition of any of statements 1-24, wherein the B ring at least one nitrogen heteroatom has is linked to the Y substituent.
26. The composition of any of statements 1-25, wherein compounds of formula IA or IB have 1-2 substituents on the B ring.
27. The composition of any of statements 1-26, wherein compounds of formula II have 0-1 substituents on the B ring.
28. The composition of any of statements 1-27, wherein p is an integer of 10-17, or 12-17, or 14-16, or 16.
29. The composition of any of statements 1-28, wherein a compound of formula II has at least 1 double bond in the $[(CH)_n]_p$ alkylene chain, each double bond separately having a cis or trans configuration.
30. The composition of any of statements 1-29, wherein a compound of formula II has at least 2 double bonds in the $[(CH)_n]_p$ alkylene chain, each double bond separately having a cis or trans configuration.
31. The composition of any of statements 1-30, wherein a compound of formula II has at least 3 double bonds in the $[(CH)_n]_p$ alkylene chain, each double bond separately having a cis or trans configuration.
32. The composition of any of statements 1-31, further comprising a carrier.

33. The composition of any of statements 1-32, further comprising a solvent.

34. The composition of any of statements 1-33, further comprising a solvent in which the compound(s) of formula IA, the compound(s) of formula 1B, the compound(s) of formula II, or a combination thereof are dissolved in the solvent.

35. The composition of any of statements 1-34, further comprising alcohol as a carrier or a solvent.

36. The composition of any of statements 1-35, further comprising ethanol as a carrier or a solvent.

37. The composition of any of statements 1-36, further comprising an emulsifier, a dispersing agent, thickening agent, a surfactant, a wetting agent of ionic or non-ionic type or a mixture of such agents 38. The composition of any of statements 1-37, wherein the compound(s) of formula I are at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm, or about 25 ppm.

39. The composition of any of statements 1-38, wherein the compound(s) of formula II are at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm.

40. The composition of any of statements 1-39, with a concentration of the compound(s) of formula I and the compound(s) of formula II of about 25 ppm.

41. The composition of any of statements 1-40, comprising one or more of the following compounds:

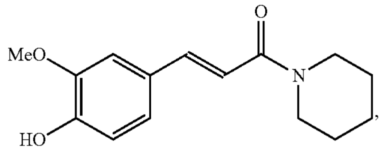,

Compound 1: $C_{15}H_{19}NO_3$
Molecular Weight: 261.32

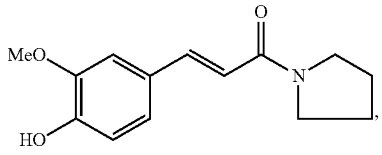,

Compound 2: $C_{14}H_{17}NO_3$
Molecular Weight: 247.29

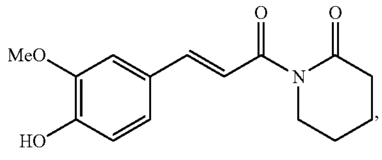,

Compound 3: $C_{15}H_{17}NO_4$
Molecular Weight: 275.30

-continued

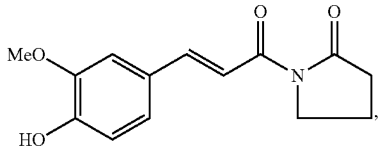,

Compound 4: $C_{14}H_{15}NO_4$
Molecular Weight: 261.28

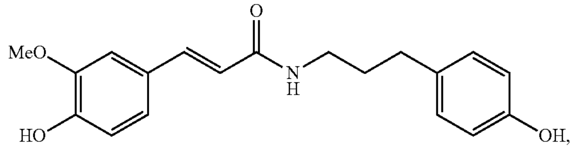,

Compound 5: $C_{19}H_{21}NO_4$
Molecular Weight: 327.38

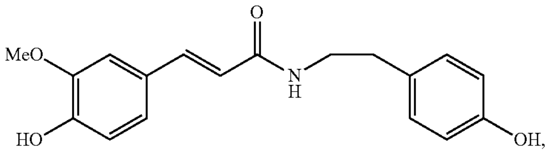, or

Compound 6: $C_{18}H_{19}NO_4$
Molecular Weight: 313.35

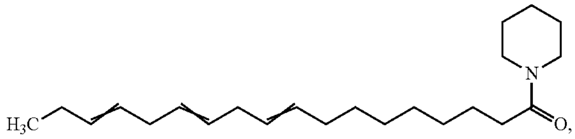, compound 7 (e.g., 1-piperdin-1-yl)octadeca-9,12,15-trien-1-one)

where the crossed double bonds ()

indicate that the double bond can have a trans or cis configuration.

42. The composition of any of statements 1-41, containing at least one compound IA with the following structure:

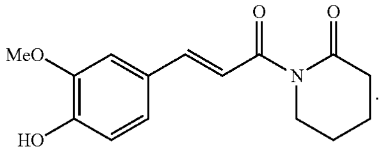.

(E)-1-(3-(4-hydroxy-3-methyoxyphenyl) acryloyl)piperidin-2-one

43. The composition of any of statements 1-42, containing at least one compound II with the following structure:

IIA

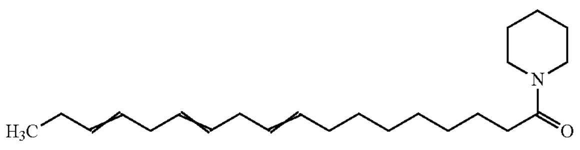

1-piperidin-1-yl)octadeca-9,12,15-trien-1-one where the crossed double bonds ()

indicate that the double bond can have a trans or cis configuration.

44. The composition of any of statements 1-43, further comprising a fungicide.
45. The composition of any of statements 1-44, further comprising a surfactant, bactericide, or a combination thereof.
46. The composition of any of statements 1-45, formulating as a paint, or cleansing solution.
47. A method comprising administering the composition of any of statements 1-46 to one or more physical structures, storage bins, plants, one or more plant seeds, or one or more plant products.
48. The method of statement 47, wherein the plants or seeds are agricultural plants/seeds, crop plants/seeds, or plants/seeds gathered from nature.
49. The method of statement 47 or 48, wherein the plant products are animal feed.
50. The method of statement 47 or 48, wherein the plant products are human food.
51. The method of any of statements 47-50, wherein the plants comprise grain-producing plants, nut-producing plants, vegetable-producing plants, fruit-producing plants, starch-producing plants, fiber-producing plants, fodder-producing plants, or a combination thereof.
52. The method of any of statements 47-51, wherein the plant products comprise grains, nuts, vegetables, fruits, starch, fibers, flour, fodder, leaves, stock, seeds, oil, or a combination thereof.
53. The method of any of statements 47-53, wherein the plant products are almonds, barley, betel nuts, brazil nuts, cashews, chestnuts, cocoanut, coffee, corn, flour, hazelnuts, macadamia nuts, oats, pecans, peanuts, pine nuts, pistachios, rice, rye, sesame seeds, soybean, spices, walnuts, wheat, or combinations thereof.
54. The method of any of statements 47-53, wherein the mycotoxin content in plants or plant products is reduced by spraying a composition onto the plants or plant products.
55. The method of any of statements 47-54, wherein the mycotoxin content in plants or plant products is reduced without inhibiting the growth of the fungi that synthesizes the mycotoxin.
56. The method of any of statements 47-55, wherein the mycotoxin content in plants or plant products is reduced by about 5%, 10%, 20%, 25%, 30%, 40%, 50%, 60%, 70%, 75%, 80%, 85%, 90%, 93%, 94%, 95%, 96%, 97%, 98%, 99%, 99.5%, or 99.9%.
57. The method of any of statements 47-56, wherein the mycotoxin content in plants or plant products is reduced to less than 50 ppm, less than 25 ppm, less than 20 ppm, less than 15 ppm, less than 10 ppm, or less than 5 ppm.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The methods and processes illustratively described herein suitably may be practiced in differing orders of steps, and the methods and processes are not necessarily restricted to the orders of steps indicated herein or in the claims. As used herein and in the appended claims, the singular forms “a,” “an,” and “the” include plural reference unless the context clearly dictates otherwise. Thus, for example, a reference to “a compound,” “a nucleic acid” or “a promoter” includes a plurality of such compounds, nucleic acids or promoters (for example, a solution of compounds or nucleic acids, or a series of promoters), and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A method for inhibiting mycotoxin production by a fungus, comprising applying a composition comprising a compound of the following formula, or a combination or salt thereof, to an object or a surface suspected of having a fungus:

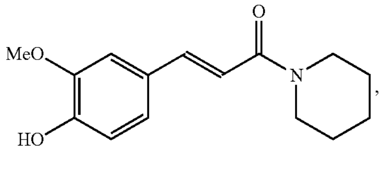,

-continued

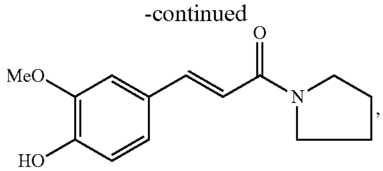

,

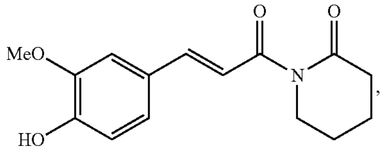

,

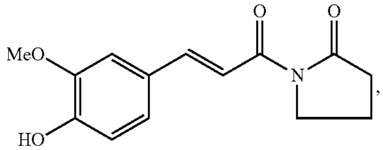

,

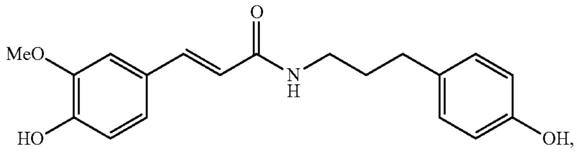

, or

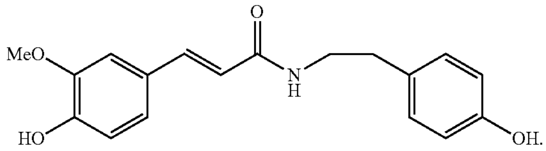

.

2. The method of claim 1, wherein the following compound is administered to an object or a surface suspected of having a fungus:

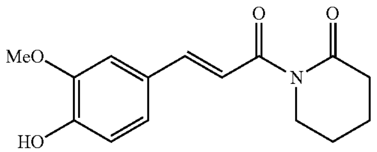

(E)-1-(3-(4-hydroxy-3-methyoxyphenyl)acryloyl)piperidin-2-one.

3. A method for inhibiting mycotoxin production by a fungus, comprising applying a composition comprising a compound of formula IA, a compound of formula IB, a compound of formula II, or a combination or salt thereof to an object or a surface suspected of having a fungus:

IA

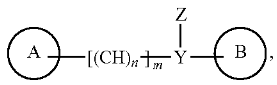

IB

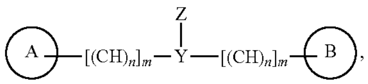

II

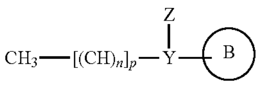

wherein:

ring A is an aryl ring that can have 1-3 substituents, each substituent in place of 1 hydrogen atom, where the substituents are each separately selected from the group consisting of oxo (=O); hydroxy; halogen; lower alkyl; lower alkoxy; amino; thiol; sulfonyl; sulfoxide; and carboxylic acid;

ring B is an aryl that can optionally have 1 or 2 substituents, where the substituents are each separately selected from: oxo (=O); hydroxy; halogen; lower alkyl; lower alkoxy; amino; thiol; sulfonyl; sulfoxide; and carboxylic acid;

Y is a methylene (CH), or a carbon atom (C);

Z is a heteroatom, hydroxy, or amino;

n is an integer equal to 1, 2, or 3;

m is an integer equal to 1, 2, 3, or 4; and p is an integer equal to any of 1-18.

* * * * *

UNITED STATES PATENT AND TRADEMARK OFFICE

CERTIFICATE OF CORRECTION

PATENT NO. : 9,988,352 B2
APPLICATION NO. : 15/316647
DATED : June 5, 2018
INVENTOR(S) : Trail et al.

It is certified that error appears in the above-identified patent and that said Letters Patent is hereby corrected as shown below:

On the Title Page

In item (*), in “Notice”, in Column 1, Line 3, delete “days. days.” and insert --days.-- therefor In Column 2, under “Other Publications”, Line 18, delete “Sevretion” and insert --Secretion-- therefor In the Claims In Column 28, Lines 11-14, in Claim 3, delete “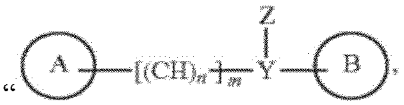” and insert -- 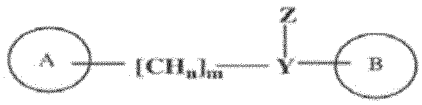

IA

-- therefor

In Column 28, Lines 18-23, in Claim 3, delete “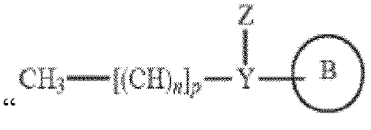” and insert

-- 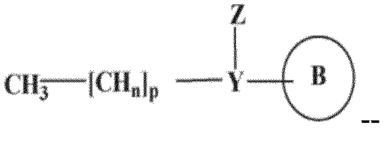 -- therefor

Signed and Sealed this
Twenty-eighth Day of May, 2019

Andrei Iancu
*Director of the United States Patent and Trademark Office*